United States Patent [19]
Jacks et al.

[11] Patent Number: 5,690,918
[45] Date of Patent: Nov. 25, 1997

[54] SOLVENT-BASED NON-DRYING LIPSTICK

[75] Inventors: Terry Jacks, Olive Branch, Miss.; Brian Mattox, Memphis, Tenn.

[73] Assignee: Maybelline, Inc., Wilmington, Del.

[21] Appl. No.: 653,230

[22] Filed: May 24, 1996

Related U.S. Application Data

[63] Continuation-in-part of Ser. No. 575,134, Dec. 19, 1995, abandoned.

[51] Int. Cl.$^6$ .................................................. A61K 7/027
[52] U.S. Cl. .................................................. 424/64; 424/401
[58] Field of Search ........................................ 424/64, 401

[56] References Cited

U.S. PATENT DOCUMENTS

| | | | |
|---|---|---|---|
| 3,406,238 | 10/1968 | Freyermuth et al. | 424/64 |
| 4,216,201 | 8/1980 | Calvo | 424/63 |
| 4,725,658 | 2/1988 | Thayer et al. | 528/15 |
| 4,760,095 | 7/1988 | Djerassi et al. | 424/64 |
| 4,897,259 | 1/1990 | Murray et al. | 424/60 |
| 5,034,216 | 7/1991 | Baume et al. | 424/64 |
| 5,039,518 | 8/1991 | Baume et al. | 424/64 |
| 5,225,186 | 7/1993 | Castrogiovanni et al. | 424/64 |
| 5,232,693 | 8/1993 | Legrow | 424/401 |
| 5,234,682 | 8/1993 | Macchio et al. | 424/63 |
| 5,505,937 | 4/1996 | Castrogiovanni et al. | 424/64 |

FOREIGN PATENT DOCUMENTS 0602905  6/1994  European Pat. Off.

*Primary Examiner*—Amy Hulina
*Attorney, Agent, or Firm*—Sherman and Shalloway

[57] ABSTRACT

A long wearing, durable, non-smearing type wax based pigmented lipstick product including volatile solvents, non-volatile silicone polymer, oil soluble liquid phase and dry powder phase, is made to have improved moisturizing properties by incorporating a mixture of moisturizers which includes essential fatty acids provided by diisoarachidyl dilinoleate, fatty acid ester of α-tocopherol, a cholesteryl/behenyl/octyldodecyl/lauroyl glutamate complex, and lauryl pyrrolidone carboxylic acid ester.

11 Claims, No Drawings

SOLVENT-BASED NON-DRYING LIPSTICK

This application is a continuation-in-part of application Ser. No. 08/575,134, filed Dec. 19, 1995, abandoned.

BACKGROUND OF INVENTION

1. Field of Invention

This invention relates to a lipstick composition and product and, more particularly, to a long wearing non-drying lipstick.

2. Problems to be Solved and Prior Art

There has been a recent trend in the cosmetic field to provide long lasting, longer wear products. In the case of lipsticks, for example, long lasting requires, among other characteristics, resistance to transfer from the lips to other surfaces such as glassware, silverware, clothing, etc. It is also important, especially in light of the long periods of time these products remain on the lips or skin, particularly for lipstick products, that the product remains moist and/or retains moisture. One attempt at such a cosmetic product having long wear characteristics is described in published European Patent Application 0602905A2 (published Jun. 22, 1994) and in corresponding U.S. Pat. No. 5,505,937. A protective lipstick product is disclosed, for example, in U.S. Pat. No. 5,093,111. In addition to waxes, oils and colorants, the lipstick composition of this patent includes, in specified proportions, cetearyl isononanoate, a sesquistearate, and isopropyl hydroxystearate. Use of fatty acid esters of α-tocopherol+(Vitamin E) as a moisturizer in cosmetic compositions is disclosed in U.S. Pat. No. 4,760,095. A lipstick formulation is shown in Example 2 of this patent.

In U.S. Pat. No. 5,288,482, it is taught that the durability of lipcare products may be increased by including an alkylmethyl polysiloxane. See also, e.g., U.S. Pat. No. 4,980,167 for a lipstick containing a silicone rubber and a silicone oil.

While the above and other patented as well as commercially available lipstick products are known which provide varying degrees of moisturization and/or long wear properties, still further improvements are desired, particularly, with regard to non-drying/moisturizing properties.

SUMMARY OF THE INVENTION

It has now been discovered that the above and other drawbacks of known lipcare products may be eliminated by including a blend of moisturizing and moisture retaining agents with other conventional lipcare product ingredients.

Accordingly, the present invention provides in a lipcare composition of the wax based non-smearing type and containing a volatile solvent and non-volatile silicone polymers, a moisturizing effective amount of a mixture of (i) diisoarachidyl dilinoleate; (ii) $C_{14}$ to $C_{22}$ fatty acid ester of alpha-tocopherol; (iii) moisture retaining emulsion stabilizing emollient, and (iv) lipophile moisturizer having delayed and remanent effect.

The preferred lipcare product may be provided in stick form, however, creams, pastes, gels, balms, lotions, and the like are also within the scope of the invention. Furthermore, the preferred lipstick compositions and products are colored lipstick cosmetic products containing cosmetically acceptable colorant, particularly solid pigments and dyestuffs.

DETAILED DESCRIPTION OF INVENTION AND PREFERRED EMBODIMENTS

The formulations disclosed herein contain cosmetically acceptable ingredients that are suitable for application to the mouth and oral cavity and which, when applied to the lips, provides long wear characteristics while moisturizing and conditioning the skin (lips).

Moisturizing Mixture

The enhancement of the moisturizing and conditioning benefits achieved by the present invention result from the incorporation of a mixture of moisturizers which are more effective and more active then moisturizer mixtures previously used in lipcare products. Moreover, this moisturizer mixture may be incorporated into the formulation in a significantly greater percentage of the formulation than was practical with prior known lipcare products.

According to the invention the moisturizer mixture includes four essential moisturizing agents: (i) diisoarachidyl dilinoleate, (ii) $C_{14}$ to $C_{22}$ fatty acid ester of alpha-tocopherol, (iii) moisture retaining emulsion stabilizing emollient; and (iv) lipophile moisturizer with delayed and remanent effect.

Each of these moisturizing ingredients will now be explained in greater detail below.

Diisoarachidyl dilinoleate is an essential moisturizing agent for the lipcare products of this invention. It is incorporated in amounts of usually from about 1 to about 20% by weight, preferably from about 4 to 15% by weight and, especially preferably, from about 10 to 13% by weight, based on the total formulation. Diisoarachidyl dilinoleate is available under the tradename LIQUIWAX DIEFA, from Brooks Industries, Inc., South Plainfield, N.J. As described in the technical literature for this product, Liquiwax Diefa is a liquid wax emollient which will soften skin without the greasiness and oiliness associated with conventional oils and esters. Liquiwax Diefa contains essential fatty acids, specifically omega-6-linoleic acid. The essential fatty acid (EFA) component helps normalize the epidermal lipid structure and promote the formation of normal healthy looking skin. Liquiwax Diefa is further described as an odorless and tasteless, clear light-colored liquid which is spreadable and has good cushion on the skin. It is recommended as a vehicle for the delivery of active topical ingredients.

In the present invention, the diiosoarachidyl dilinoleate moisturizing ingredient may also function as an oil soluble liquid component as discussed in further detail below.

The preferred fatty acid ester of alpha-tocopherol is tocopheryl linoleate. However, any of the alpha-tocopherol esters disclosed in U.S. Pat. No. 4,760,095, the disclosure of which is incorporated herein by reference thereto, may be used in this invention.

The amount of the alpha-tocopherol ester moisturizing ingredient may range from about 0.1 to about 10% by weight, preferably from about 0.5 to about 5% by weight; based on the total formulation. A more preferred range is from about 0.6 to about 2% by weight of the total formula.

The third essential moisturizing ingredient is the moisture retaining emulsion stabilizing emollient. A particular preferred emollient is cholesteryl/behenyl/octyldodecyl/lauroyl glutamate complex, available under the tradename Eldew CL-301, a product of Ajinomoto U.S.A., Inc., Teaneck, N.J.

This glutamate complex is a petroleum-like wax at room temperature and melts rapidly at human body temperature. It is derived from L-glutamic acid, lauric acid and three alcohols (cholesterol, 2-octyldodecanol and behenol) and may be characterized by the formula

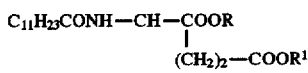

where R and R¹ represent, individually, cholesteryl, 2-octyldodecyl, behenyl. The ratios of the three alcohols may be varied widely but, generally, such ratios would be nearly equimolar, such as, for example, from 10 to 60 mole % for each of the alcohols, although higher or lower ratios could be used according to need. Moreover, other similar alcohols may be used in place of some or all of one or more of cholesterol, 2-octyldodecanol, and behenol, so long as its water absorbing and retaining capacity is not significantly impaired.

In addition to its high water holding capacity, Eldew CL-301 is stated to have high moisture permeability (e.g. to perspiration) to allow excess moisture to evaporate freely from the skin surface. Eldew CL-301 also is characterized by its ability to improve dispersion of pigments in make-up and other color cosmetics.

While the glutamic acid complex is the preferred moisture retaining emulsion stabilizing emollient other suitable materials may be used in place of or in addition to the glutamic acid complex, such as, for example, pyrrolidone carboxylic acid (PCA) glyceryl oleate, dipalmitoylhydroxyproline, cetearylglucoside, Polyolprepolymer-2, Petrolatum, caprylic/capric/stearic triglyceride, Shea Butter, cholesterol, lecithin, phospholipids, Illipe Butter, and the like.

The moisturizing additive (iii) is incorporated in an amount of from about 0.1 to about 10% by weight, preferably from about 0.5 to about 5% by weight, and especially preferably from about 0.6 to about 2% by weight based on the total weight of the composition.

Moisturizing additive (iv) is included in the moisturizing mixture because of its long lasting moisturizing capacity, namely, its delayed and remanent effect. That is, the moisturizing additive (iv) exerts its effects over a number of hours, e.g. up to about 24 hours, rather than as an instant reaction.

Particularly preferred as the remanent moisturizer is the lauric ester of pyrrolidone carboxylic acid,

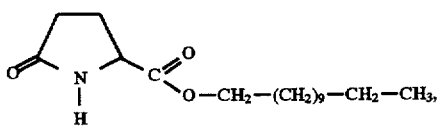

which is known as lauryl PCA and is available under the trademark Laurydone® from Usines Chimiques D'Ivry-LA-Bataille (UCIB).

Other lipophilic moisturizers which may be used in place of or in addition to Lauryl PCA include, for example, Lauryl Methyl PCA, phytoglycolipids, cholesterol, glycosphingolipids, palmitoyl hydrolyzed milk protein, Illipe Butter, and the like.

The amount of the lipophilic moisturizer (iv) in the subject lipcare products will usually be from about 0.1 to 10% by weight, preferably from about 0.5 to 6% by weight, more preferably from about 1 to 4% by weight, based on the total composition.

The mixture of the moisturizing ingredients will be incorporated into the lipcare product in an amount of from about 2 to 30%, preferably from about 6 to 25%, and especially preferably from about 10 to 20% by weight of the composition.

Moreover, within the general and preferred amounts of the individual moisturizers, these four ingredients are typically present at a mixing weight ratio of (i):(ii):(iii):(iv) in the range of from about 10:0.1–4:0.1–4:0.1–4, more preferably from about 10:0.5–2:0.5–2:0.5–3. Although, as evident from the above, certain moisturizing ingredients may be able to fulfill the functions of both (iii) and (iv), it is preferred that if other than the preferred glutamate complex for (iii) and tauryl PCA for (iv) are used, different moisturizers be selected for the (iii) and (iv) components.

Volatile Solvent

The volatile solvent contributes to the wear characteristics of the lipcare composition. Preferably, the composition includes a mixture of two or more volatile solvents, one each of volatile silicone solvents and volatile hydrocarbon solvents.

A preferred example of volatile silicone solvent is cyclomethicone. Other examples include the cyclic silicone fluids available from, for example, Dow Corning Co. and General Electric Co., under such tradenames as DC 200 Fluid, SF 1204, SF 1202 and SF 1173. Generally, the viscosities of the volatile silicone solvent is in the range of from about 0.5 and up to about 20 centistokes at 25° C., preferably up to about 10 centistokes at 25° C. Representative examples of volatile or low-viscosity silicone liquids include both the cyclic and linear silicones such as disclosed, for example, in U.S. Pat. Nos. 5,505,937, 5,118,507, 4,578, 206, and 4,855,129, the disclosures of which are each incorporated herein by reference thereto.

Examples of the volatile hydrocarbon solvent include isododecane and C8–20 isoparaffins, preferably $C_8$–$C_{16}$ isoparaffins especially C8–12 isoparaffins. Normal alkanes may also be used, alone, or in admixture with, the isoparaffins (isoalkanes). Isododecane is especially preferred.

Weight ratios of the volatile silicone/volatile hydrocarbon in the range of from about 10:1 to 1:10 are generally suitable. A more preferred ratio is from about 6:1 to 1:2. Furthermore, total amounts of the volatile solvents may range from about 1 to 68% of the composition. However, a more preferred range is from about 33 to 59%, especially from about 40 to 50% by weight of the total lipcare composition.

Non-Volatile Silicone Polymer

The non-volatile silicone polymer component also contributes to the wear properties of the lipcare formulations. The silicone polymers are characteristically non-volatile, particularly in comparison to the above-described volatile silicone component. The silicone polymers are often solid resinous or gummy materials but, generally, are relatively high molecular weight non-volatile solid, semisolid or waxy, or liquid materials.

One class of useful silicone polymers are silicone ester waxes, such as those disclosed in U.S. Pat. Nos. 5,505,937, 5,334,737 and 4,725,658, the disclosures of which are incorporated herein in their entireties by reference thereto. Specific examples of these silicone ester waxes include diisostearyl trimethylolpropane siloxy silicate and lauryl trimethylolpropane siloxy silicate.

Another class of non-volatile silicone polymer useful in the lipstick cosmetic product of this invention includes polyalkyl siloxanes wherein the alkyl groups have from 1 to about 22 or more carbon atoms, typically with a viscosity in the range of from about 10 and up to about 10,000,000 centistokes (Cs), preferably in the range of from about 10 to 100,000 Cs, at 25° C. These materials may be provided in various physical forms, such as, high viscosity liquids, wax-like solids and liquids, gum-like, resinous, etc. Preferably, the polyalkylsiloxane is a polysiloxane polyalkylene copolymer, e.g., an alkylmethylsilicone or polysiloxane represented by the formula

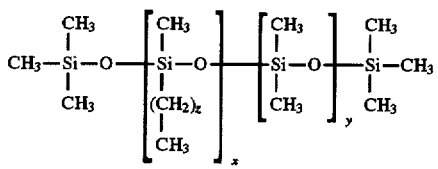

where x has a value, on average, of 1–300, y has a value, on average, of 1–50, and z has a value, on average, of 5–50. Preferably, x has value in the range of 3–40; y has a range of 2–190; and z has a range of 5–30, especially 8–20. Such alkylmethylsilicone copolymers are described in, for example, U.S. Pat. No. 5,288,482 and patents cited therein, the disclosures of which are incorporated herein in their entirety by reference thereto. The alkylmethylsilicone copolymers are also commercially available from various sources, such as Dow Chemical Co. and Goldschmidt Chemical Corp. of Hopewell, Va. under the Abil®-Wax tradename; e.g., Abil-Wax 9800 is stearyl dimethicone and Abil-Wax 9801 is cetyl dimethicone, which are, respectively, available in waxy and liquid forms at about room temperature (e.g., 25° C. or lower).

Amounts of the silicone polymer are generally in the range of from about 0.5 to 16% by weight, preferably from about 1 to 12% by weight, and especially preferably 1.5 to 8% by weight, based on the total composition.

Wax

The lipcare products of this invention, especially when in stick form, will typically include one or more waxes, including natural waxes and synthetic wax-like materials. Suitable waxes have a melting point in the range of from about 32° to 120° C., more preferably 40° to 110° C. Any of the waxes normally used in cosmetic and lipcare products may be used in this invention.

Examples of suitable waxes include paraffin, ozokerite, cerein wax, microcrystalline wax, candelilla wax, carnauba wax, beeswax, cetyldimethicone, and low molecular weight polyolefin waxes, such a ethylene/propylene copolymers, polyethylene, etc. Mixtures of two or more of natural and synthetic waxes will generally and preferably be used to achieve desired characteristics, such as body, spreadability, long-wear, and the like.

The wax component will normally be present in an amount within the range of from about 5 to 35%, preferably from about 8 to 30%, and more preferably from about 12 to 20%, by weight, based on the total composition.

Oil Phase

Oily (oil soluble) liquids are included in the subject lipcare products to provide desirable feel, spreadability, gloss and other desirable characteristics. Preferably, a mixture of low viscosity (generally from about 5 or 10 centipoises (cps) at 25° C., and up to about 100 cps, preferably up to about 50 cps, at 25° C.) and high viscosity (at least about 100 cps, preferably at least about 150 cps (at 25° C.) and up to about 10,000, preferably up to about 1,000 cps (at 25° C.)). Typically, the oil soluble liquids are esters that are carboxylic or alcoholic in nature. Representative of a low viscosity oil soluble liquid having a viscosity in the range of 5 to 15 cps at 25° C. is isononyl isononanoate. Other suitable low viscosity oils include, for example, octyl palmitate, diioctylmaleate, octyldedecanol, PEG-4 diheptanoate, isononylnonoate, coco-dicaprylate/caprate, polyglyceryl-3-diisostearate, cetyl alcohol, isocetyl alcohol, oleyl alcohol, cetyl acetate, acetylated lanolin alcohol, and the like.

As examples of high viscosity oil soluble liquids mention may be made of, for example, polyvinylpyrrolidone (PVP)/hexadecene and trioctyldodecyl citrate, with viscosities in the range of 100 to 1,000 cps at 25° C. Other triesters of citric acid, such as disclosed in U.S. Pat. No. 5,244,665, the disclosure of which is incorporated herein by reference thereto, may be used in place of some or all of trioctyldodecyl citrate. Diisoarachidyl dilinoleate, one of the essential moisturizing ingredients of this invention, also functions as a high viscosity oily liquid (100–1,000 cps at 25° C.) and, therefore, the amount of this moisturizing ingredient should also be included in the amount of the oil phase components.

Other examples of high viscosity oils useful in the present invention include lanolin oil, sesame seed oil, glyceryl trioctanoate, tridecyl trimellitate, castor oil, gaprylic/capric triglyceride, corn oil, mineral oil, hydrogenated polyisobutene, and polybutene. See also EPO 602 902A2 for other suitable low and high viscosity oils.

The ratio of low viscosity to high viscosity oils in the oil phase is preferably in the range of from 1:10 to 20:1, more preferably 1:8 to 16:1, especially preferably 1:2 to 10:1. More particularly, the ratio of low and high viscosity oils should be selected to provide the oil phase with a viscosity in the range of from about 750 to 950 cps at 25° C. The total amount of the oil phase will generally fall within the range of 2 to 35% by weight, preferably 5 to 30% by weight and especially preferably from about 10 to 20% by weight of oil phase based on the total composition.

Powder Phase

In order to provide a colored product or a product having adequate texture and coverage of the lips the formulation of this invention will include a dry powder phase distributed throughout the product as is typical in most lipcare, especially lipstick, products.

Suitable powders may be pigmented, pearlized, or non-pigmented and mixtures of these types may be used. Examples of non-pigmented powders include bismuth oxychloride, titanated mica, titanium dioxide, mica and acrylate copolymers. The use of acrylate copolymer powder is advantageous because of its good binding properties for other ingredients in the composition. As examples of pigmented powders mention may be made of organic and inorganic pigments, generally referred to as lakes or oxides of metallic salts of certified color additives, such as, for example, D & C and F, D & C blues, reds, yellows, browns and oranges. Other examples of non-pigmented powders include boron nitride, kaolin, aluminum starch octenylsuccinate, polymethylmethacrylate beads, silica, nylon, zinc stearate, talc and amino acids.

The amount of powder phase will be selected to provide the desired texture, binding, coverage and coloration to the formula but, generally, will be within a range of from about 2 to 15% by weight, preferably 5 to 15% by weight, based on the total composition. Within these total amounts it is generally preferred that the amount of pigmented powder falls within the range of from about 1 to 14%, preferably about 3 to 13% and the amount of non-pigmented powder falls within the range of from about 1 to 5%, preferably from about 1 to 4%, based on the total composition.

Other Ingredients

Any of the other aesthetic or functional ingredients normally used in lipcare products may also be included in the compositions of this invention. Examples of such additional ingredients include, for example, preservatives, antioxidants, and the like. The amounts of such other additives may be freely chosen so long as the amounts can achieve the desired function without impairing the overall properties and moisturizing characteristics of the inventive compositions. Examples of preservatives and antioxidants useful in this invention include the parabens, such as isopropylparaben, isobutylparaben, butylparaben, propylparaben and methylparaben; tocopherol, TBHQ, BHA and BHT. Usually, antioxidants and preservatives may be incorporated in amounts generally within the range of 0.2 to 1.0% by weight, preferably 0.3 to 0.8% by weight of the total composition.

Formulation

Generally, any of the techniques well known in the art may be used to mix the various essential and non-essential ingredients presented in the formulations of this invention.

For example, the cosmetically acceptable ingredients of the formulation may be combined by first grinding a portion of the pigmented and non-pigmented dry powder with a portion of the oil soluble liquids. Next, the wax(es), remainder of the oil soluble liquids and non-volatile silicone polymer are added together under heat and mixed. The remainder of the dry powder is added and mixed followed by addition of the volatile solvents. The moisturizers may be added last. After continued mixing of the total ingredients until homogeneous, the resulting mixture is poured into molds and allowed to cool.

More particularly, the pigmented dry powder and a portion of the oil soluble liquids are passed through a triple roll mill. The waxes, silicone polymer and remainder of oil soluble liquids are heated at about 125° C. using an appropriate size kettle equipped with a stirrer. The remainder of the dry powders are added to the molten mixture while continuing stirring. The volatile solvents are then added to the kettle mixture for further mixing and finally, after cooling the mixture, the moisturizers are added while mixing is continued until the ingredients are homogeneously distributed. The homogeneous mixture may be transferred to molds and cooled to form the desired shaped products.

The invention will now be described by the following illustrative but non-limitative examples.

EXAMPLE 1

Using the procedure described above the following lipstick product is prepared:

| Ingredient | Amount (wt %) |
| --- | --- |
| Cyclomethicone | 30.25 |
| Synthetic Wax | 12.50 |
| Isododecane | 12.00 |
| Diisoarachidyl Dilinoleate[1] | 10.21 |
| Stearyl Dimethicone | 6.40 |
| Diisostearyl trimethylolpropane siloxy silicate | 5.00 |
| Paraffin Wax | 4.51 |
| Isononyl isononanoate | 2.50 |
| Ozokerite Wax | 2.00 |
| Trioctyldodecyl citrate | 1.00 |
| Alpha-tocopherol linoleate | 1.00 |
| Cholesteryl/Behenyl/Octyldodecyl/ Lauroyl Glutamate[2] | 1.00 |
| Lauryl PCA[3] | 2.00 |
| PVP Hexadecene Copolymer | 0.50 |
| Acrylate Copolymer | 0.50 |
| Pigmented Powder | 7.80 |
| Non-pigmented Powder | 0.23 |
| Preservatives[4] | 0.60 |

[1]as Liquiwax Diefa
[2]as Eldew CL-301
[3]as Laurydone ®
[4]Isopropyl paraben, isobutylparaben, n-butylparaben

EXAMPLE 2

| Ingredient | Amount (wt %) |
| --- | --- |
| Cyclomethicone | 34.50 |
| Isododecane | 10.00 |
| Ozokerite | 2.00 |
| Paraffin | 4.51 |
| Ethylene/Propylene Copolymer | 10.00 |
| Stearyl Dimethicone | 1.50 |
| Isononyl isononanoate | 1.00 |
| Trioctyldodecyl citrate | 1.00 |
| Diisoarachidyl dilinoleate[1] | 10.34 |
| PVP Hexadecene | 0.50 |
| Diisostearyl Trimethylolpropane Siloxy Silicate | 4.75 |
| Preservatives[4] | 0.40 |
| α-Tocopherol | 0.10 |
| Lauryl PCA[2] | 2.00 |
| α-Tocopherol linoleate | 1.00 |
| Cholesteryl/Behenyl/Octyldodecyl/ Lauroyl Glutamate[3] | 1.00 |
| Acrylate copolymer | 0.50 |
| Red 7 Calcium Lake | 2.00 |
| Red 6 Barium Lake | 8.00 |
| Yellow 5 Aluminum Lake | 1.00 |
| Titanium dioxide | 0.50 |
| Titanium dioxide/mica | 0.70 |
| Titanium dioxide/mica/iron oxide | 0.70 |
| Bismuth chloride | 2.00 |

[1]as Liquiwax Diefa
[2]as Eldew CL-301
[3]as Laurydone ®
[4]Isopropyl paraben, isobutylparaban, n-butylparaben Following the procedures generally outlined above this formulation is prepared by grinding the pigmented portion (Red 7, Red 6 and Yellow 5) of the dry powder ingredients with the oil soluble liquids (isononylisononanoate, trioctyldodecyl citrate, diisoarachidyl dilinoleate, PVP/hexadecene); the silicone resin diisostearyl trimethylolpropane siloxy silicate); and preservatives (isopropyl paraben, isobutyl paraben, n-butyl paraben, α-tocopherol). tocopherol). The waxes (ozokerite, paraffin, ethylene/propylene copolymer, stearyl dimethicone) are added with heating. After the waxes are melted and the ingredients well mixed, the remainder of the dry powder (titanium dioxide-mica-iron oxide; bismuthoxychloride, acrylate copolymer) are added. The volatile solvents (cyclomethicone, isododecane) are added next, and while the mixture is further stirred and slightly cooled, the remainder of the moisturizing ingredients (α-tocopherol linoleate, glutamate complex, lauryl PCA) are added with stirring. After the mixture becomes homogeneous it is poured into lipstick molds and left to cool. The tops are scraped and left to chill before removing from the mold.

Lipstick samples prepared according to Example 2 were compared to a commercial non-transfer type lipstick in a blind comparison panel test in which the subjects were regular lipstick users. The panelists were asked to compare the moisturizing, look, wear, durability and feel characteristics of both products (neither of which was identified to the panelists). By a ratio of more than 3 to 1 (with about one-half expressing no preference) the panelists overall favored the lipstick of Example 2 over the commercial product at 3 hours after application. After 4 hours, 6 hours and 8 hours both products were comparable.

EXAMPLE 3

Following procedures as generally described above, lipstick products with the following compositions are prepared:

| Ingredient | Amount (wt. %) | | |
|---|---|---|---|
| | A | B | C |
| Cyclomethicone | 34.50 | 34.50 | 34.50 |
| Isododecane | 10.00 | 10.00 | 10.00 |
| PVP Hexadecene Copolymer | 0.50 | 0.51 | 0.50 |
| Stearyl Dimethicone | 4.25 | 1.53 | 1.50 |
| Ethylene Propylene Copolymer | 11.00 | 12.89 | 11.00 |
| Ozokerite | 3.00 | 2.58 | 3.00 |
| Paraffin Wax | 4.51 | 5.81 | 4.51 |
| Isononyl Isononanoate | 1.00 | 1.00 | 1.00 |
| Trioctyldodecyl Citrate | 1.00 | 1.00 | 1.00 |
| Preservative | 0.40 | 0.40 | 0.40 |
| Titanium Dioxide | 2.00 | 2.00 | 2.00 |
| Pigments[1] | 9.17 | 9.17 | 9.17 |
| Acrylates Copolymer | 0.50 | 0.50 | 0.50 |
| Diisoarachidyl Dilinoleate | 9.50 | 9.50 | 9.50 |
| Duochrome YR | 1.94 | 1.94 | 1.94 |
| Biron ESQ | 1.45 | 1.45 | 1.45 |
| Tocopheryl Linoleate | 1.00 | 1.00 | 1.00 |
| Cholesteryl/Behenyl/octyldodecyl/Lauroyl Glutamate | 1.00 | 1.00 | 1.00 |
| Lauryl PCA | 2.00 | 2.00 | 2.00 |
| Diisoarachidyl Dilinoleate | 1.49 | 1.43 | 4.24 |
| Tocopherol | 0.10 | 0.10 | 0.10 |

[1]Mixture of Red 6, Red, 7, Red Oxide, Yellow Oxide, Blue 1, Yellow 5, Yellow 6.

The above formulation "A" was subjected to a panel test to test the transfer resistance of formulation "A" and to compare transfer resistance to the user's "regular lipstick." Two tests were carried out by a panel of regular lipstick users. In both tests each panelist applied the lipstick of formulation "A" which was allowed to set for thirty minutes. In the first test each of 50 panelists lightly dabbed her lips with a supplied white cloth. When asked if an acceptable amount of lipstick remained on her lips 49 (98%) of the panelists answered "yes." In response to the question of whether an insignificant or a significant amount of lipstick "came off" on the cloth 47 (94%) replied that an insignificant amount came off. Finally each panelist was asked if the amount which came off on the cloth was "less than," "equal to" or "greater than" the amount that comes off with her regular lipstick. 46 (92%) said the amount was less than the amount that comes off with regular lipstick while 2 each replied that an "equal amount" or "greater amount" came off than comes off with regular lipstick. It is noted that of the 50 panelists approximately 15 different products from approximately ten different manufacturers were listed as the regularly used lipstick.

In the second panel test with 46 of the 50 subjects from the first panel test, each panelist again applied formulation "A" and allowed the lipstick to set for 30 minutes. Each panelist then drank water from a glass or cup. After drinking, the subjects evaluated the products for (1) whether an "acceptable" amount of lipstick remained on the lips after drinking (100% said "yes"); (2) whether the amount that "came off" on the glass or cup was significant (98% (45) said the amount was "insignificant"); and (3) whether the amount that "came off" was a) "less than", b) "greater than" or c) "equal to" the amount that comes off with her regular lipstick (Replies: 96% (44) "less than"; 4% (2) "equal to" and 0% "greater than").

This Example demonstrates that a lipstick formulation without a silyl ester wax but containing only conventional lipstick waxes, i.e., stearyl dimethicone, synthetic wax (ethylene/propylene copolymer), ozokerite wax, and paraffin wax, provides acceptable long wear and transfer resistant properties and, in addition, provides excellent moisturization.

What is claimed is:

1. In a wax based non-smearing solid pigment containing colored lipstick cosmetic product containing volatile solvent and non-volatile silicone polymer, the improvement comprising a moisturizer mixture comprising moisturizing effective amounts of (i) diisoarachidyl dilinoleate;

(ii) $C_{14}$ to $C_{22}$ fatty acid ester of alpha-tocopherol;

(iii) moisture retaining emulsion stabilizing emollient selected from the group consisting of cholesteryl/behenyl/octyldodecyl/lauroyl glutamate complex, pyrrolidone carboxylic acid, glyceryl oleate, dipalmitoylhydroxyproline, cetearylglucoside, polyprepolymer-2, petrolatum, caprylic/capric/stearic triglyceride, Shea butter, cholesterol, lecithin, phospholipids, and Illipe butter; and (iv) lipophile moisturizer having delayed and remanent effect selected from the group consisting of lauryl pyrrolidone carboxylic acid ester, lauryl methyl pyrrolidone carboxylic acid ester, phytoglycolipids, cholesterol, glycosphingo-lipids, palmitoyl hydrolyzed milk protein, and Illipe Butter.

2. The lipstick cosmetic product of claim 1 wherein the moisturizer mixture comprises, based on the total product, on a weight basis, (i) from about 1 to 20% diisoarachidyl dilinoleate, (ii) from about 0.1 to 10% $C_{14}$ to $C_{22}$ fatty acid ester of alpha-tocopherol, (iii) from about 0.1 to 10% of said emollient and (iv) from about 0.1 to 10% by weight of said lipophile moisturizer.

3. The lipstick cosmetic product of claim 1 wherein (ii) the fatty acid ester of alpha-tocopherol comprises vitamin E linoleate.

4. The lipstick cosmetic product of claim 1 wherein (iii) comprises a glutamic acid complex of the formula

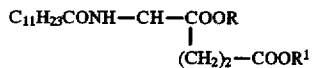

$$C_{11}H_{23}CONH-CH-COOR$$
$$|$$
$$(CH_2)_2-COOR^1$$

wherein R and $R^1$, independently represent a mixture of cholesteryl, 2-octyldodecyl and behenyl.

5. The lipstick cosmetic product of claim 1 wherein the moisturizer component (iv) comprises lauryl pyrrolidone carboxylic acid ester.

6. The lipstick cosmetic product of claim 1 comprising from about 2 to 50% by weight of volatile silicone solvents, from about 10 to 45% by weight of cosmetic wax, from about 6 to 20% of volatile hydrocarbon solvent, from about 0.5 to 16% by weight of non-volatile silicone polymer, from about 4 to 40% by weight powder and pigments, and from about 5 to 30% by weight of moisturizer mixture.

7. The lipstick cosmetic product of claim 1 comprising from about 25 to 42% by weight of volatile silicone solvent;

from about 6 to 22% by weight volatile hydrocarbon solvent;

wherein the total amount of volatile silicone solvent and volatile hydrocarbon solvent is from about 33 to by weight;

from about 8 to 30% by weight cosmetically acceptable wax;

from about 1 to 12% by weight non-volatile silicone polymer, from about 5 to 15% by weight dry powder comprising pigment and non-pigment powders; and from about 6 to 25% by weight of the moisturizer mixture.

8. The lipstick product of claim 1 comprising in approximate amounts by weight:

| | |
|---|---|
| cyclomethicone | 30–35% |
| isododecane | 8–14% |
| synthetic wax | 10–20% |
| mixture of low viscosity and high viscosity oil soluble liquids | 8–16% |
| non-volatile silicone polymer | 1.5–8% |
| preservatives | 0.1–1% |
| dry powder comprising pigmented and non-pigmented solids | 5–15% |
| moisturizing mixture | 11–16% | wherein the moisturizing mixture comprises, in percent by weight, based on the total weight of product,

| | |
|---|---|
| diisoarachidyl dilinoleate | 9–13% |
| α-tocopherol linoleate | 0.8–1.2% |
| cholesteryl/behenyl/octyldodecyl/ lauroyl glutamate | 0.8–1.2% |
| Lauryl PCA | 0.5–4% | and wherein the amount of diisoarachidyl dilinoleate is included in the amount of the mixture of low viscosity and high viscosity oil soluble liquids.

9. The lipstick cosmetic product of claim 1 wherein the moisture retaining emollient (iii) is different than the lipophile moisturizer (iv).

10. The lipstick cosmetic product of claim 1 wherein the mixing weight ratio of the moisturizer mixture (i):(ii):(iii):(iv) is 10:0.1–4:0.1–4:0.1–4.

11. The lipstick cosmetic product of claim 1 wherein the mixing weight ratio of the moisturizer mixture (i):(ii):(iii):(iv) is 10:0.5–2:0.5–2:0.5–3.

* * * * *